United States Patent
Tang et al.

(10) Patent No.: US 9,668,724 B2
(45) Date of Patent: Jun. 6, 2017

(54) SYSTEMS AND METHODS FOR PERCUTANEOUS SUTURE DELIVERY

(71) Applicant: MEDEON Biodesign, Inc., Taipei (TW)

(72) Inventors: Hsiao-Wei Tang, Taipei (TW); Yu-Shih Weng, Taipei (TW); Shih-Jui Han, Taipei (TW); Chung-Chu Chen, Taipei (TW); Chao C. Chen, Edison, NJ (US)

(73) Assignee: Medeon Biodesign, Inc., Taipei (TW)

( * ) Notice: Subject to any disclaimer, the term of this patent is extended or adjusted under 35 U.S.C. 154(b) by 491 days.

(21) Appl. No.: 14/186,246

(22) Filed: Feb. 21, 2014

(65) Prior Publication Data

US 2014/0249552 A1    Sep. 4, 2014

Related U.S. Application Data

(60) Provisional application No. 61/768,344, filed on Feb. 22, 2013, provisional application No. 61/781,973, (Continued)

(51) Int. Cl.
*A61B 17/04* (2006.01)
*A61B 17/00* (2006.01)
(Continued)

(52) U.S. Cl.
CPC ...... *A61B 17/0469* (2013.01); *A61B 17/0057* (2013.01); *A61B 2017/00367* (2013.01); (Continued)

(58) Field of Classification Search
CPC .... A61M 25/04; A61B 17/04–17/0485; A61B 17/057;
(Continued)

(56) References Cited

U.S. PATENT DOCUMENTS 5,964,773 A    10/1999  Greenstein
6,036,699 A *   3/2000  Andreas ............ A61B 17/0057
                                                      606/139
(Continued)

FOREIGN PATENT DOCUMENTS

WO    2005112789 A2    12/2005
WO    2011112721 A1     9/2011

OTHER PUBLICATIONS

International Search Report dated May 14, 2014 in corresponding PCT Application No. PCT/US2014/017813.
(Continued)

*Primary Examiner* — Victor Nguyen
*Assistant Examiner* — Jonathan Hollm
(74) *Attorney, Agent, or Firm* — Dergosits & Noah LLP; Todd A. Noah

(57) ABSTRACT

Systems and methods are provided for percutaneously suturing tissue. An elongated deployment member having a guide member coaxially disposed over a shaft member may be used to carry a needle deployment member. The needle deployment member may be carried at a distal end of the elongated deployment member and include a plurality of needles releasably secured to the needle deployment member, wherein each needle is routed coaxially within the distal end of the needle deployment member. The needle deployment member may further include a needle pusher driven by a link coaxially disposed within the shaft member, wherein the needle pusher is configured to advance each needle through the distal end of the needle deployment member and coaxially over the proximal end of the needle deployment member to position the plurality of needles at a piercing angle in a proximal direction.

20 Claims, 12 Drawing Sheets

Related U.S. Application Data filed on Mar. 14, 2013, provisional application No. 61/824,267, filed on May 16, 2013, provisional application No. 61/843,724, filed on Jul. 8, 2013, provisional application No. 61/874,057, filed on Sep. 5, 2013.

(51) Int. Cl.
*A61B 17/22* (2006.01)
*A61B 17/29* (2006.01)
*A61B 90/00* (2016.01)

(52) U.S. Cl.
CPC ............... *A61B 2017/00663* (2013.01); *A61B 2017/00986* (2013.01); *A61B 2017/047* (2013.01); *A61B 2017/0472* (2013.01); *A61B 2017/22069* (2013.01); *A61B 2017/2912* (2013.01); *A61B 2017/2925* (2013.01); *A61B 2017/2927* (2013.01); *A61B 2090/0811* (2016.02)

(58) Field of Classification Search
CPC ................... A61B 2017/047–2017/048; A61B 2017/00637–2017/00641; A61B 2017/00663–2017/00668

USPC ...... 606/8, 139, 144–150, 198; 604/104–109
See application file for complete search history.

(56) References Cited

U.S. PATENT DOCUMENTS

| | | | |
|---|---|---|---|
| 6,280,460 B1* | 8/2001 | Bolduc | A61B 17/0469 606/144 |
| 6,464,707 B1* | 10/2002 | Bjerken | A61B 17/0469 606/139 |
| 6,896,685 B1* | 5/2005 | Davenport | A61B 17/0057 606/139 |
| 7,879,049 B2* | 2/2011 | Dillon | A61B 17/0057 606/139 |
| 2012/0296373 A1 | 11/2012 | Roorda et al. | |
| 2013/0165956 A1* | 6/2013 | Sherts | A61B 17/0482 606/148 |
| 2013/0178872 A1* | 7/2013 | Shriver | A61B 17/0057 606/148 |

OTHER PUBLICATIONS

Written Opinion dated May 14, 2014 in corresponding PCT Application No. PCT/US2014/017813.

* cited by examiner

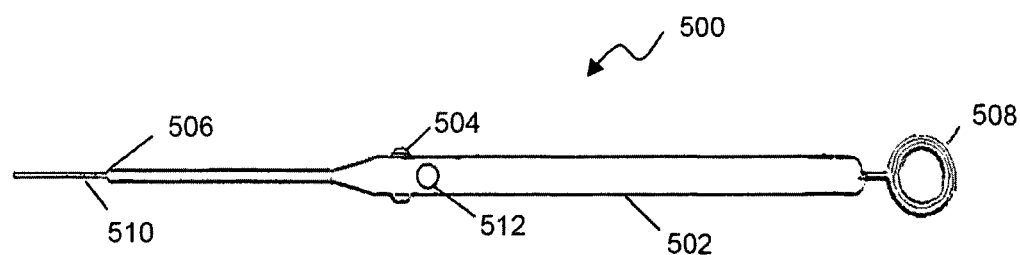
FIG. 25
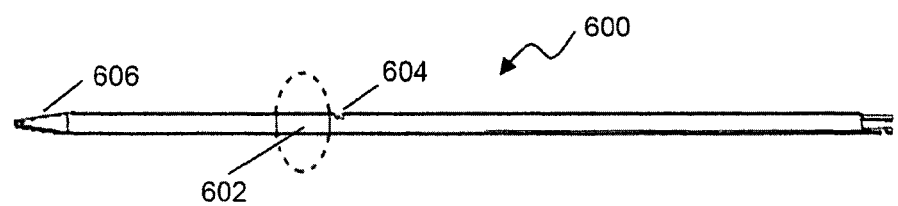
FIG. 27
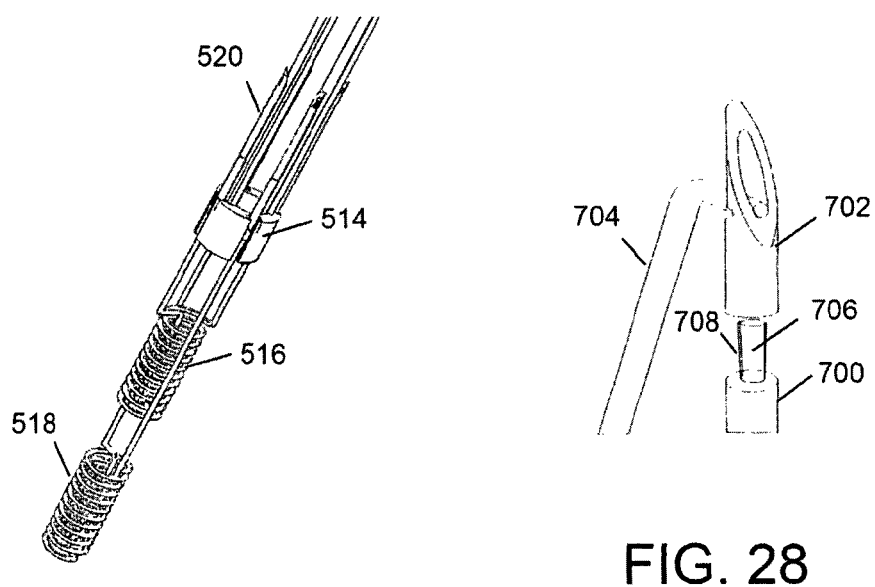
FIG. 28
FIG. 26

SYSTEMS AND METHODS FOR PERCUTANEOUS SUTURE DELIVERY

RELATED APPLICATIONS

This application claims priority to and benefit of U.S. Provisional Patent Application Ser. No. 61/768,344, filed Feb. 22, 2013; U.S. Provisional Patent Application Ser. No. 61/781,973, filed Mar. 14, 2013; U.S. Provisional Patent Application Ser. No. 61/824,267, filed May 16, 2013; U.S. Provisional Patent Application Ser. No. 61/843,724, filed Jul. 8, 2013 and U.S. Provisional Patent Application Ser. No. 61/874,057, filed Sep. 5, 2013, the contents all of which are incorporated by reference in their entirety.

FIELD OF THE PRESENT DISCLOSURE

The present disclosure relates generally to techniques and devices for closing openings in a patient's vasculature or other body lumens. For example, the present disclosure relates to systems, devices, and methods for percutaneous suturing of arterial and venous puncture sites to approximate tissue around the opening, such as may be required following a surgical procedure.

BACKGROUND

To improve recovery time, a variety of interventional and diagnostic procedures may be carried out in a minimally invasive manner by accessing a desired location within a patient's body percutaneously. By introducing catheters or other elongated devices into the vasculature at a convenient entry point, such procedures may be performed at a remote location by guiding the device through the body lumen to the desired position. Although these techniques represent less impact on the patient than conventional open procedures, access to the vasculature requires forming an opening in an artery or vein that subsequently must be repaired.

A variety of methods may be used to close the access opening. Conventionally, hemostasis may be achieved through manual compression to substantially reduce the flow of blood through the opening and allow clot formation. Although generally successful, compression may be take a significant amount of time and may be associated with considerable patient discomfort. Additionally, complications such as unintended total occlusion of the lumen that may result in ischemia or thrombosis can occur. These aspects may be exacerbated depending upon the size of the opening necessary to introduce the percutaneous device, whether anticoagulants are employed and on the condition of the patient.

To ameliorate these problems, techniques for suturing the opening to achieve hemostasis and reduce time to ambulation have been developed. In order to maintain the minimal invasiveness of the procedure, many of these techniques are adapted to be performed percutaneously. For example, the suture delivering device may be introduced through the same opening used to perform the procedure. Typically, one or more needles are deployed by the suture delivering device to pierce the vessel wall and draw the suture material through so that the suture may be secured over the adventitial surface and close the opening. Despite the benefits associated with the use of suture delivering devices, a number of challenges exist. In particular, it is desirable for the needle or needles to be positioned accurately with respect to the vessel wall so as to pierce the tissue far enough away from the opening to result in a sufficiently robust location for the suture. It is also desirable to provide a device configured to deploy and actuate the needles in a reproducible manner to minimize the amount of skill required from the operator. Accordingly, this disclosure is directed to systems and methods for percutaneously suturing an opening in a body lumen while providing these and other desired characteristics.

SUMMARY

This disclosure includes a suture delivery device for percutaneously suturing tissue. The suture delivery device may include an elongated deployment member having a guide member coaxially disposed over a shaft member, a needle deployment member carried at a distal end of the elongated deployment member. The needle deployment member may include a lower band configured to retain a non-piercing end of each of the plurality of needles and an upper band configured to position the plurality of needles at the piercing angle when the lower band is actuated by a trigger mechanism. The trigger mechanism includes a trigger link between the needle pusher and a trigger in the handle portion of the device such that the triggering of the trigger mechanism causes the needle pusher to push the needles towards a needle catcher or needle receiver located at the distal end of the elongated deployment member. The trigger link may include one or more linking mechanisms between the needle pusher and the needle catcher/receiver. In this embodiment, the needle deployment member comprises a needle pusher, at least one needle, a needle pusher linker, an upper band and a lower band. The needle pusher may be relatively distal end to lower band. The needle pusher and needle linker are contained at the distal end of needle deployment member.

In other words, the needle deployment member may include a needle pusher configured to retain a non-piercing end of each of the plurality of needles that is separate from the lower band. The needle pusher can also be the same structure as the lower band. In the embodiment where the plurality of needles is retained in the needle pusher, the lower band serves as a guide for the plurality of needles to prevent the needles from dislodging or buckling. When the needles are lifted, the needles extend underneath the lower band and travel over the upper band causing the needles to protrude out at an angle. The angle of the needle lifting may be adjusted by the distance between upper band and lower band before needle lifting. The angle of the needle lifting may also be adjusted by changing the diameter of the upper band.

Alternatively, the needle deployment member may also include a plurality of or at least one deflectable wings, wherein a proximal end of the needle deployment member is secured to the guide member and a distal end of the needle deployment member is secured to the shaft member and a plurality of needles releasably secured to the needle deployment member. The needle deployment member may transition between an uncompressed configuration corresponding to a first distance between the proximal and distal ends that longitudinally aligns the plurality of needles with the shaft member and a compressed configuration corresponding to a second distance between the proximal and distal ends that positions the plurality of needles at a piercing angle in a proximal direction, the first distance being greater than the second distance.

In one aspect, relative longitudinal movement of the shaft member with respect to the guide member may transition the needle deployment member between the uncompressed and compressed configurations. Further, each of the deflectable wings may have a slot configured to carry one of the plurality of needles. In addition, the needle deployment member may have a lower band configured to retain a non-piercing end of each of the plurality of needles and an upper band configured to position the plurality of needles at the piercing angle when in the compressed configuration.

In another aspect, the elongated deployment member may also have a sheath member coaxially disposed over the guide member, such that the sheath member may extend over a proximal portion of the plurality of needles positioned at the piercing angle when the sheath member is advanced distally over the guide member. Further, the elongated deployment member may also include a catcher member coaxially disposed between the guide member and the sheath member, such that the catcher member captures the plurality of needles positioned at the piercing angle when the catcher member is advanced distally over the guide member.

As desired, the suture delivery device may have a housing at a proximal end of the elongated deployment member that provides relative longitudinal movement between the guide member and each of the sheath member, the catcher member and the shaft member. The housing may be configured to store a reproducible amount of tension that may be selectively released to simultaneously move the sheath member distally with respect to the guide member and the shaft member proximally with respect to the guide member.

In yet another aspect, the suture delivery device may have a suture catheter secured to the distal end of the elongated delivery member, wherein the suture catheter carries suture material that may be threaded through the plurality of needles. Additionally, the suture catheter may be secured to the elongated delivery member by a hinge allowing rotation in one direction.

This disclosure also includes methods for delivering a suture percutaneously. For example, a suitable method may include providing an elongated deployment member having a guide member coaxially disposed over a shaft member, a needle deployment member carried at a distal end of the elongated deployment member, the needle deployment member. In one aspect, the needle deployment member may include a lower band configured to retain a non-piercing end of each of the plurality of needles and an upper band configured to position the plurality of needles at the piercing angle when the lower band is actuated by a trigger mechanism. The trigger mechanism includes a needle pusher linker that links the needle pusher and a trigger in the handle portion of the device such that the triggering of the trigger mechanism causes the needle pusher to push the needles towards a needle catcher or needle receiver located at the distal end of the elongated deployment member. The needle pusher linker may include one or more linking mechanisms between the needle pusher and the needle catcher/receiver. In this embodiment, the needle deployment member comprises a needle pusher, at least one needle, a needle pusher linker, an upper band and a lower band. The needle pusher may be relatively distal end to lower band. The needle pusher and needle pusher linker are contained at the distal end of needle deployment member.

The needle deployment member may further include a plurality of deflectable wings, wherein a proximal end of the needle deployment member is secured to the guide member and a distal end of the needle deployment member is secured to the shaft member and a plurality of needles releasably secured to the needle deployment member, advancing the elongated deployment member percutaneously to a desired position in a patient and withdrawing the shaft proximally relative to the guide member to transition the needle deployment member from an uncompressed configuration that longitudinally aligns the plurality of needles with the shaft member to a compressed configuration that extends the deflectable wings positions the plurality of needles at a piercing angle in a proximal direction.

In one aspect, the elongated deployment member may also have a sheath member coaxially disposed over the guide member, such that advancing the sheath member distally over the guide member to extend over a proximal portion of the plurality of needles positioned at the piercing angle to cause the plurality of needles to pierce tissue sandwiched between the extended deflectable wings and a distal end of the sheath. Advancing the sheath member distally over the guide member and withdrawing the shaft member proximally within the guide member may be performed simultaneously. Further, advancing the sheath member distally and withdrawing the shaft member proximally may be performed by applying an automatically reproducible amount of force.

In another aspect, the elongated deployment member may also have a catcher member coaxially disposed between the guide member and the sheath member, such that the catcher member may be advanced distally over the guide member to capture the plurality of needles positioned at the piercing angle. In addition, the needles may be captured by friction between the distal end of the sheath and a distal end of the catcher member.

In yet another aspect, the shaft member may be advanced distally with respect to the guide member after the plurality of needles is captured to transition the needle deployment member to the uncompressed configuration. Further, the sheath member and the catcher member may be withdrawn proximally with respect to the guide member after the plurality of needles is captured.

Additionally, suture material may be carried in a suture catheter secured to the distal end of the elongated delivery member, wherein the suture material is threaded through each of the plurality of needles. Further, withdrawing the sheath member and the catcher member may draw the suture material through the tissue.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which:

FIG. 25 depicts an alternative suture delivery device, according to one embodiment;

FIG. 26 depicts a needle pushing element, according to one embodiment; and

FIG. 27 depicts an alternative catheter with a balloon expandable distal region, according to one embodiment;

FIG. 28 depicts a needle tip and base assembly, according to one embodiment;

DETAILED DESCRIPTION

Figure 1:
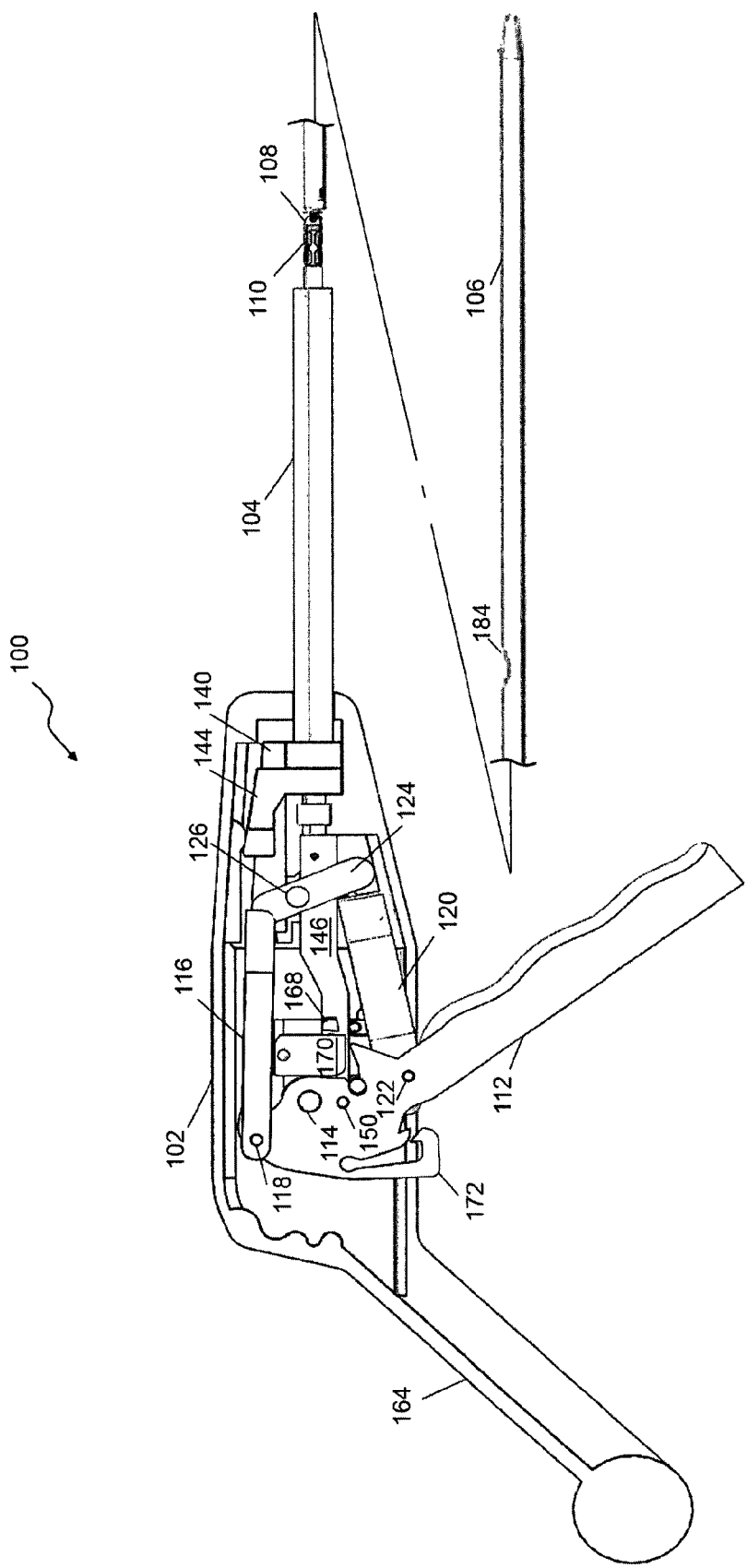
FIG. 1 depicts a partial sectional view of a suture delivery device, according to one embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains. For example, the term "suturing" includes drawing two surfaces or edges together with a flexible material to close a puncture, opening, or other wound, wherein the suture is a material that may be synthetic or natural, such as a polymer, gut, metallic wire or other suitable equivalents.

Finally, as used in this specification and the appended claims, the singular forms "a, "an" and "the" include plural referents unless the content clearly dictates otherwise.

According to this disclosure, a device for applying sutures percutaneously to promote hemostasis following an interventional procedure may generally include a distal, reconfigurable region that exhibits a reduced insertion profile and an expanded profile for stabilizing tissue during delivery of the sutures. Relative movement between a proximal region of the device and the expanded profile region may allow tissue to be secured between the regions and provide a target for needle-deployed sutures carried by the device. As will be appreciated from the discussions below, the relative movement between the distal region and the proximal region may involve movement of the distal region towards the proximal region, movement of the proximal region towards the distal region, or both. Further, the suture delivery devices of this disclosure may provide coordinated and/or automatic operation steps involved in the placement of the sutures, including one or more of the deployment of the distal region, deployment of the proximal region, securing tissue between the distal and proximal regions, firing of the needles to place the sutures and capture of the needles after passing through the secured tissue.

Figure 29:
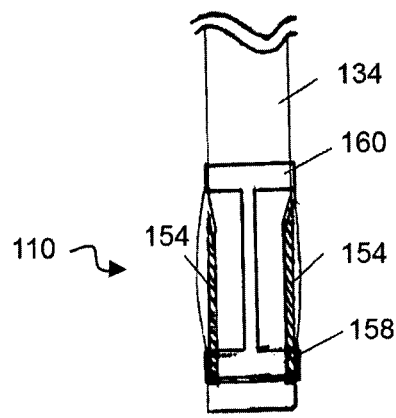
FIG. 29 depicts an embodiment of the needle deployment member without deflectable wings.
Figure 30:
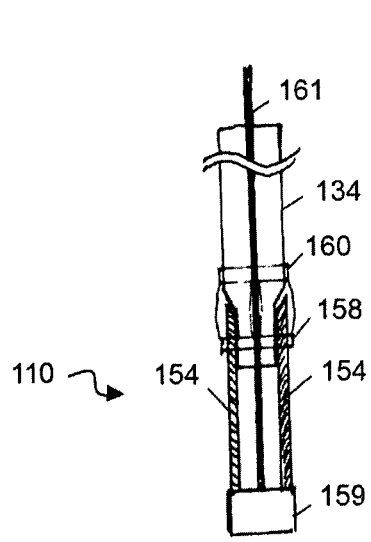
FIG. 30 depicts an alternative embodiment of the needle deployment member without deflectable wings.
Figure 31:
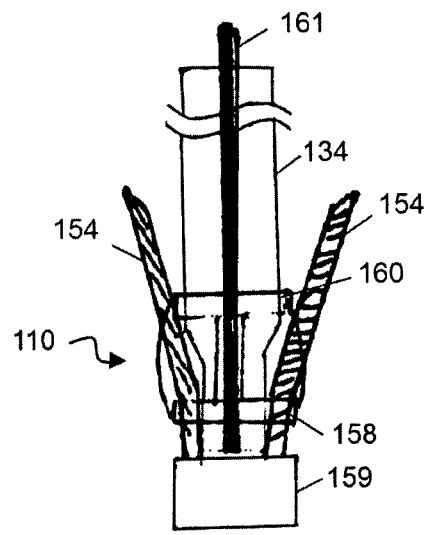
FIG. 31 depicts the needle deployment member shown in FIG. 30 after the needles have been fired.

FIGS. 1-15 and 19 illustrate an embodiment of the invention wherein the needle deployment member 110 includes a plurality of deflectable wings. However, as further described herein and shown in FIGS. 29-31, the needle deployment member 110 does not need to have a plurality of deflectable wings in addition to a needle pusher 159, a plurality of needles 154, a needle pusher linker 161, an upper band 160 and a lower band 158. In this embodiment, the needle deployment member may include a lower band 158 configured to retain a non-piercing end of each of the plurality of needles 154 and an upper band 160 configured to position the plurality of needles at the piercing angle when the needle pusher 159 is actuated by a trigger mechanism linked to the needle pusher linker 161. The trigger mechanism includes a needle pusher linker 161 between the needle pusher 159 and a trigger in the handle portion of the device (not shown in FIGS. 29-31) such that the triggering of the trigger mechanism causes the needle pusher 159 to push the needles 154 towards a needle catcher or needle receiver (not shown) located at the distal end of the elongated delivery member 104. The needle pusher linker 161 may include one or more linking mechanisms between the needle pusher 159 and a trigger in the handle portion of the device. In this embodiment, the needle deployment member 110 comprises a needle pusher 159, at least one needle, a needle pusher linker 161, an upper band 160 and a lower band 158. The needle pusher 159 may be relatively distal to lower band 158. The needle pusher 159 and needle pusher linker 161 may be contained at the distal end of needle deployment member 110.

In an embodiment, the needle pusher 159 and needle pusher linker 161 may be at distal end of the needle deployment member 110 wherein the distance between the upper band 160 and the lower band 158 varies or remains relatively constant during operation. In other words, the piecing of the tissue by the needles is driven by needle pusher 159, which is linked to the proximal end of the device by needle pusher linker 161. During needle piercing, the distance between upper band 160 and lower band 158 may be constant or may decrease. The needle pusher 159 may be separate from the lower band 158 and located distal to the lower band 158. In another embodiment, the needle pusher 159 and needle pusher linker 161 may be at distal end of the shaft 134 wherein the distance between the upper band 160 and the lower band 158 varies or remains relatively constant during operation. In other words, the piecing of the tissue by the needles 154 is driven by needle pusher 159, which is linked to the proximal end of the device by needle pusher linker 161. During needle piercing, the distance between upper band 160 and lower band 158 may be constant or may decrease. In this embodiment, the needle pusher 159 may be separate from the lower band 158 and located distal to the lower band 158. The needle pusher 159 can also be located adjacent to the lower band 158, depending upon the length of the needles 154 used. See FIGS. 29 and 30. One skilled in the art can readily determine the distance between the needle pusher 159 and the lower band 158 in the embodiments wherein the lower band 158 does not also act as the needle pusher 161.

To summarize, in an embodiment the needle deployment member may include a needle pusher configured to retain a non-piercing end of each of the plurality of needles that is separate from the lower band. The needle pusher can also be the same structure as the lower band. In the embodiment where the plurality of needles is retained in the needle pusher, the lower band serves as a guide for the plurality of needles to prevent the needles from dislodging or buckling. When the needles are lifted, the needles extend underneath the lower band and travel over the upper band causing the needles to protrude out at an angle. The angle of the needle lifting may be adjusted by setting initial distance between upper band and lower band. The angle of the needle lifting may also be adjusted by changing the diameter of the upper band.

Aspects of this disclosure will now be described in the context of an embodiment shown in FIG. 1. Suture delivery device 100 includes housing 102, an elongated delivery member 104 and a distal suture catheter 106 for carrying the suture material. In this embodiment, suture catheter 106 is joined to the distal end of delivery member 104 through hinge 108, that may offer rotation in one direction of up to approximately 90°. Needle deployment member 110 is positioned at the distal end of delivery member 104, proximal to suture catheter 106. Housing 102 includes handle 112 that pivots on axle 114 to drive actuator 116 through pin 118 as well as charge spring 120, which is connected at opposing ends to handle 112 by pin 122 and to lever 124, which pivots on axle 126. As will be described below, interoperation between handle 112, actuator 116 and lever 124 cooperate to sequentially deploy, pierce and capture suture carrying needles using needle deployment member 110.

Figure 2:
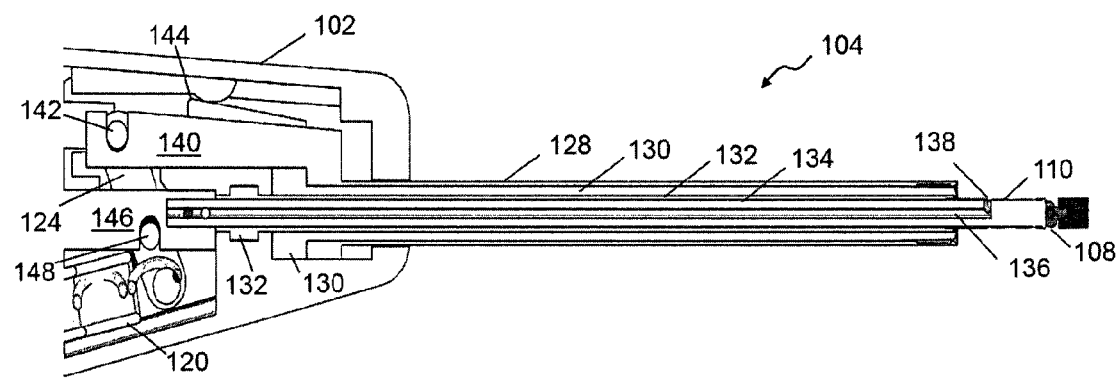
FIG. 2 depicts a detail view of the suture delivery device of FIG. 1.

Further details regarding delivery member 104 are shown in the partial detail view of FIG. 2. In this embodiment, delivery member 104 includes an outer tubular sheath 128, coaxially disposed over tubular catcher 130, which in turn is coaxially disposed over tubular guide 132 that is coaxially disposed over shaft 134. Shaft 134 may include bleed back lumen 136 having a distal port 138 and a proximal port 140. As known in the art, position of delivery member 104, and correspondingly needle deployment member 110, within an artery may be indicated by pulsatile blood flow that enters at distal port 138, is conducted through lumen 136 and may be visualized when it exits at proximal port 140. Sheath extension 140 is coupled to lever 124 by pin 142, catcher extension 144 is engaged by actuator 116 depending upon the position of handle 112 and shaft extension 146 is coupled to lever 124 by pin 148.

Returning to FIG. 1, pin 150 on handle 112 may engage shaft extension 146. Accordingly, sheath 128, catcher 130 and shaft 134 may move axially with respect to each other and housing 102 depending upon the motion of handle 112 and lever 124, while guide 132 remains stationary with respect to housing 102.

Figure 3:
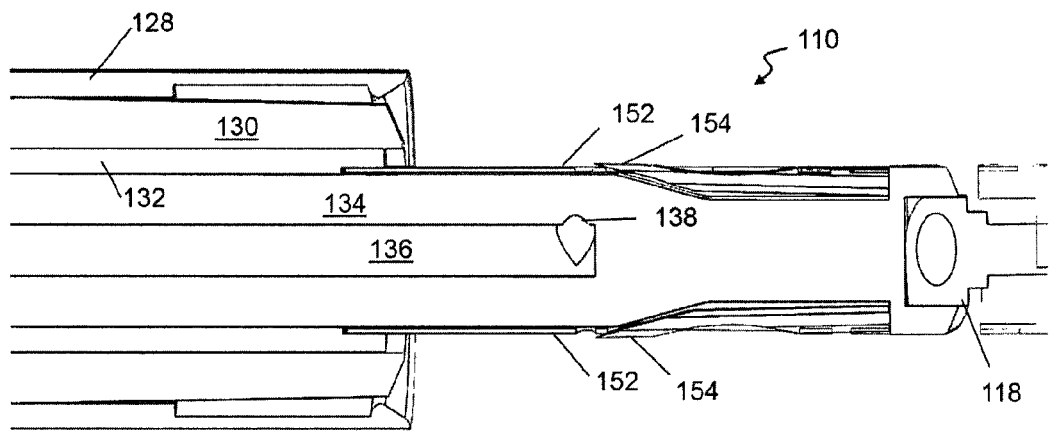
FIG. 3 depicts a further detail view of the suture delivery device of FIG. 1.

A more detailed view of the distal end of delivery member 104 is shown in FIG. 3. Needle deployment member 110 is coupled at its proximal end to guide 132 and at its distal end to shaft 134. Relative movement between shaft 134 and guide 132 axially compresses needle deployment member 110 and causes wings 152 to deflect outwards, extending away from shaft 134, while needles 154 are positioned at an angle configured to pierce the tissue of the vessel wall around the opening. Suitable angles may be in the range of approximately 14-20° with respect to shaft 134. In one embodiment, the angle may be approximately 16.3°.

Figure 4:
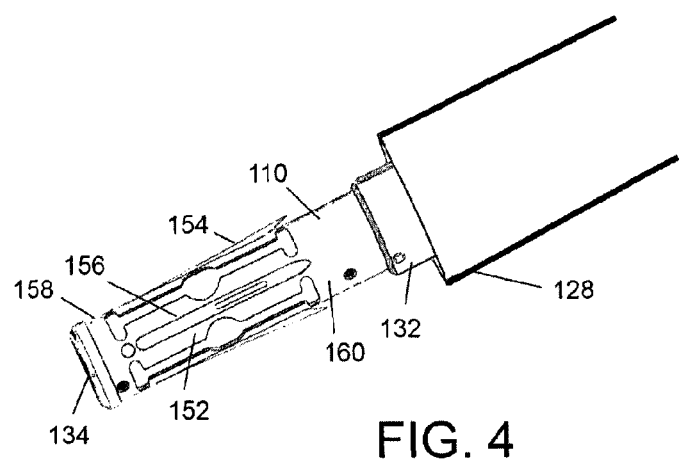
FIG. 4 depicts a needle deployment member in an uncompressed configuration, according to one embodiment.
Figure 5:
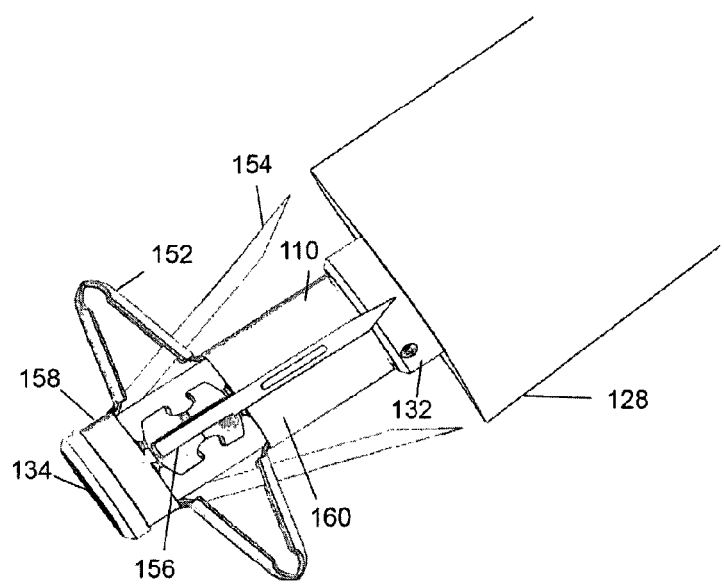
FIG. 5 depicts a needle deployment member in a compressed configuration, according to one embodiment.
Figure 6:
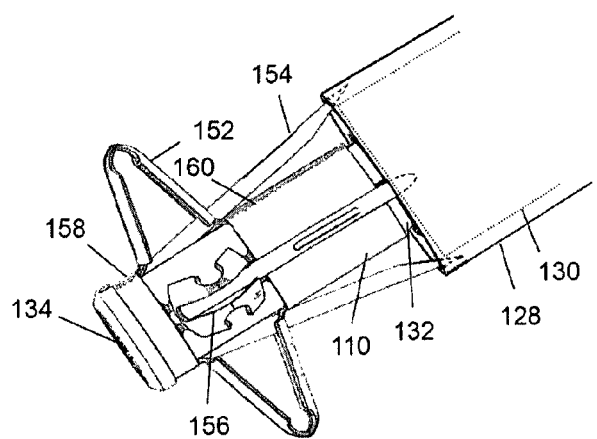
FIG. 6 depicts a sheath being extended over needles positioned at a piercing angle by a compressed configuration of the needle deployment member, according to one embodiment.

FIGS. 4-6 show a sequence representing compression of needle deployment member 110 to position needles 154 at the desired piercing angle and subsequent capture of needles 154 by friction between sheath 128 and catcher 130.

Starting with FIG. 4, needle deployment member 110 is shown in its uncompressed configuration, representing a maximal distance between the distal ends of shaft 134 and guide 130. Needles 154 are retained axially within slots 156 formed in deflectable wings 152 and releasably secured at their base by lower band 158 of needle deployment member 110. In one aspect, a desired amount of retention force may be imparted to needles 154 by friction with lower band 158. For example, lower band 158 may be configured to contact a sufficient surface area of needles 154 to provide retention. Alternatively, or in addition, the force with which lower band 158 engages needles 154. Thus, retention of needles 154 may be achieved by any desired combination of interaction between needles 154 and lower band 158 and/or slots 156.

Next, FIG. 5 shows needle deployment member 110 in its compressed configuration, achieved by longitudinally withdrawing shaft 134 relative to guide 130. As shown, wings 152 deflect outwards, while upper band 160 at the proximal end of slot 156 engages and lifts needles 154 into their piercing angle. A desired piercing angle may also be achieved by adjusting the configuration of needles 154 to control their interaction with upper band 160. Accordingly, relative motion between upper band 160 and lower band 158 may be used to position needles 154 at an appropriate piercing angle. As will be appreciated, the relative motion between upper band 160 and lower band 158 may be achieve by moving lower band 158 towards upper band 160, by moving upper band 160 towards lower band 158, or both. For example, upper band 160 and lower band 158 have been described as elements of needle deployment member 110. However, in embodiments that employ a different expanding distal region design, upper band 160 and lower band 158 may be provided as independent elements subject to proximal control to position needles 154 at the desired piercing angle.

In one aspect, deformation areas of wings 152 may be designed at functional structure points. The strain may be managed by the thickness and curvature of slot 156 to lie below its plastic deformation zone, which may be in the range of 6-8%. Lower band 158 holds needles 154 within slots 156. The degree to which needles 154 are retained in may be adjusted by varying the height of lower band 158 as described above. The piercing angle may be adjusted by varying the distance between lower band 158 and upper band 160 when needle deployment member 110 is compressed.

Then, as shown in FIG. 6, sheath 128 may be advanced over the proximal sharp ends of needles 154, sandwiching the tissue of the vessel wall against outwardly deflected wings 152. As will be appreciated, needles 154 are deployed automatically at the desired angle and interaction between wings 152 and sheath 128 provide reproducible conditions for piercing the tissue of the vessel wall. Needles 154 may be captured by friction between the inner surface of sheath 128 and the outer surface of catcher 130. In the embodiment shown in FIG. 1, sheath 128 is configured with an annular rib 162 configured to increase engagement with needles 154 and augment the capture force provided by sheath 128 and catcher 130.

As described above, the devices of this disclosure may be used to close and facilitate repair of openings created during intravascular procedures. For example, the Seldinger technique is a known procedure for accessing the femoral artery and suture delivery device 100 may be used to close the opening created in the artery. More generally, the devices of this disclosure may be used for percutaneous delivery of sutures for closing various sizes of vascular access site, and reducing the time to hemostasis and time to ambulation of patients who have undergone catheterization procedures using sheaths in the range of 5 F-24 F. Still more generally, this disclosure is applicable to any clinical procedure involving closure of incisions or orifices of soft tissues and organs. For example, suture delivery device 100 or an embodiment suitably adapted may be used for closure of soft tissue opening or tear in surgical or interventional procedures such as gastrointestinal perforation, perforated ulcer, closure of trocar incision associated with minimally invasive or natural orifice transluminal endoscopic surgery, closure of patent foramen ovale (PFO), spinal annular repair, and other procedures that may benefit from percutaneous suturing.

Further details of the disclosure may be appreciated in the context of exemplary methods for using suture delivery device 100. One embodiment is represented by corresponding sequences of handle positions and needle deployment member configuration that are depicted in FIGS. 7-18.

Figure 7:
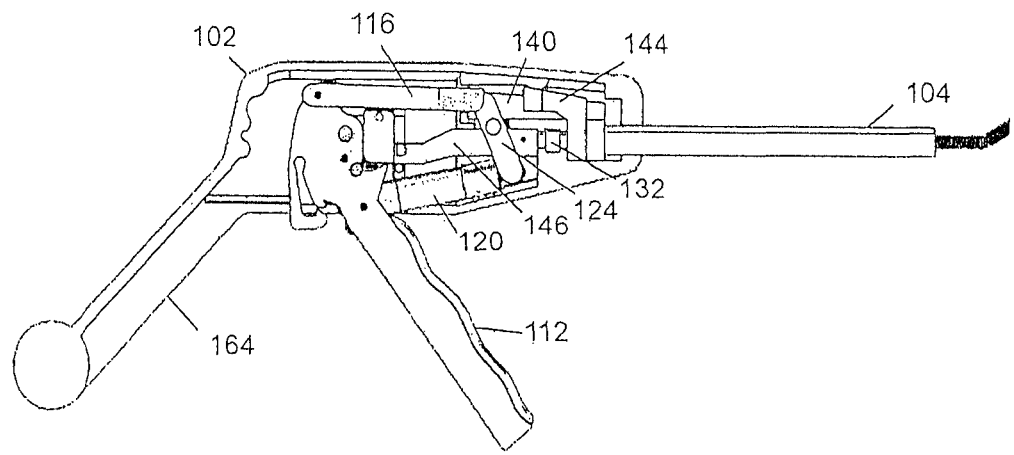
FIG. 7 depicts a housing and handle configuration in an initial state, according to one embodiment.
Figure 8:
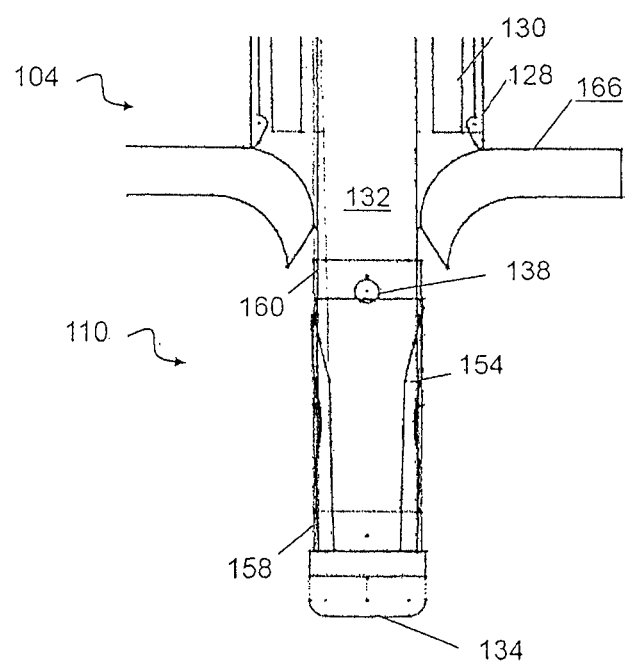
FIG. 8 schematically depicts the configuration of the needle deployment member in the initial state, according to one embodiment.

An initial state of suture delivery device 100 and position of handle 112 is shown in FIG. 7 and the corresponding configuration of needle deployment member 110 is shown in FIG. 8. As can be seen in FIG. 7, handle 112 begins at a rightmost position that is extended away from grip 164. In this configuration, sheath extension 140 and catcher extension 144 are located at the proximal edge of their respective ranges of travel so that sheath 128 and catcher 130 are correspondingly at their most proximal position with respect to guide 132. Shaft extension 146 is at the distal edge of its range of travel, positioning shaft 134 in its most distal position with respect to guide 132. As a result, needle deployment member 110 is in the uncompressed state shown in FIG. 8. For clarity, the suture catheter 106 portion of suture delivery device 100 is not shown in the sequence of figures. The distal end of delivery member 104 has been advanced to a location within a patient's vasculature, through an opening in tissue wall 166. In this embodiment, distal port 138 provides fluid communication to bleed back lumen 136, allowing visualization of pulsatile blood flow to confirm an appropriate position of needle deployment member 110 within a patient's artery. The position of shaft 134 in its distal position with respect to guide 132 corresponds to the greatest relative distance between lower band 158 and upper band 160 of needle deployment member 110. Needles 154 are positioned against shaft 134 for insertion.

Figure 9:
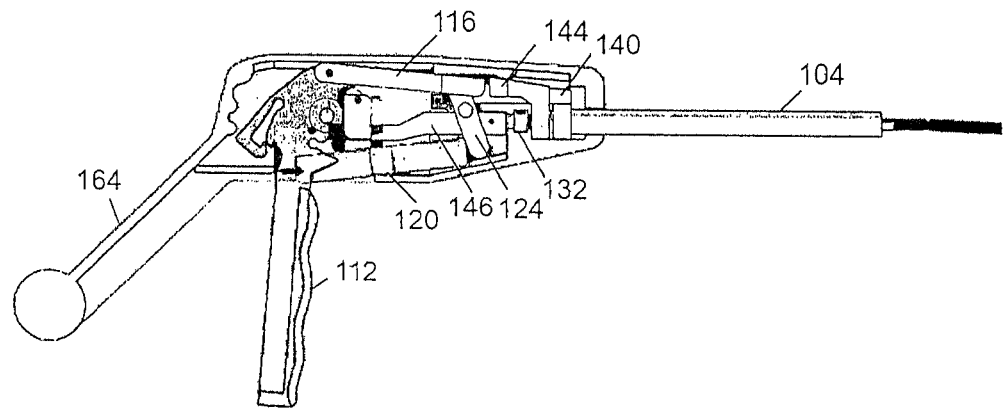
FIG. 9 depicts a housing and handle configuration during spring charging, according to one embodiment.
Figure 10:
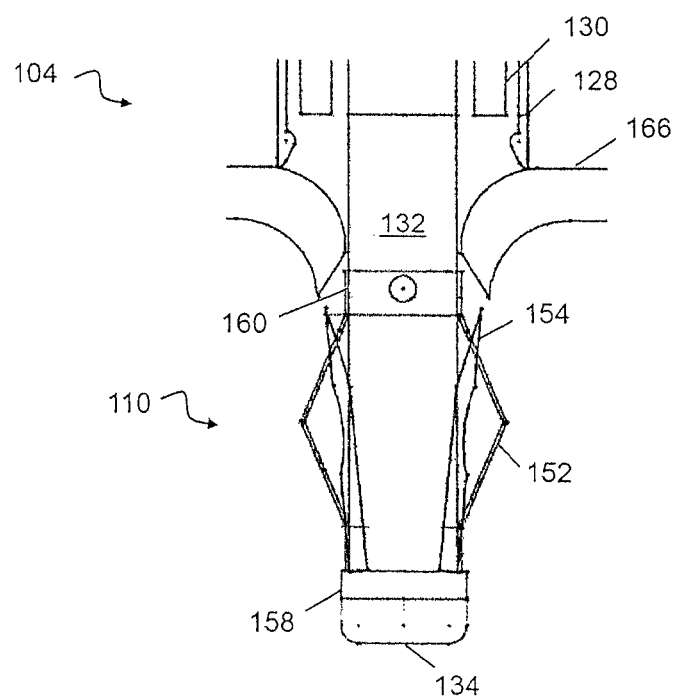
FIG. 10 schematically depicts the configuration of the needle deployment member in a pre-compressed state, according to one embodiment.

Next, FIG. 9 shows suture delivery device 100 as handle 112 is drawn towards grip 164. Extension of spring 120 charges it, but actuator 116 has not yet engaged catcher extension 144. Further, in this embodiment, stop 168 on shaft extension 146 engages release button 170, preventing relative movement of shaft 134 in the distal direction. As described above, lever 124 is coupled to shaft extension 146 through pin 148, such that motion of lever 124 is also restrained. If desired, stop 168 may be configured to allow some amount of distal travel of shaft 134 before it engages release button 168, resulting in a pre-compression of needle deployment member 110 as shown in FIG. 10. The amount of distal travel allowed to shaft 134 with respect to guide 132 causes a relative decrease in the distance between lower band 158 and upper band 160. Correspondingly, wings 152 begin to deflect outwardly from shaft 134 and needles 154 begin to travel from their insertion profile to the piercing angle. The pre-compressed configuration may help maintain position of needle deployment member 110 within the body lumen as the increased diameter resists withdrawal from the opening in tissue wall.

Figure 11:
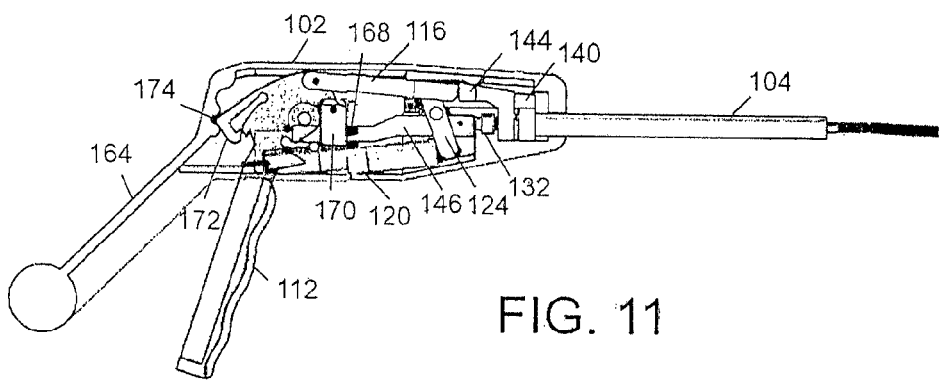
FIG. 11 depicts a housing and handle configuration after spring charging, according to one embodiment.

Handle 112 may then be drawn towards grip 164 to achieve the fully cocked configuration shown in FIG. 11. Pawl 172 engages detent 174 in this position, providing the user with tactile feedback indicating that a reproducible amount of tension has been applied and stored in spring 120. The configuration of pawl 172 resists motion of handle 112 away from grip 164 before completion of the procedure. Since stop 168 engages release button 170, further relative movement of shaft 134, sheath 128 or catcher 130 does not occur. Correspondingly, no changes in the configuration of needle deployment member 110 occur after pre-compression.

Figure 12:
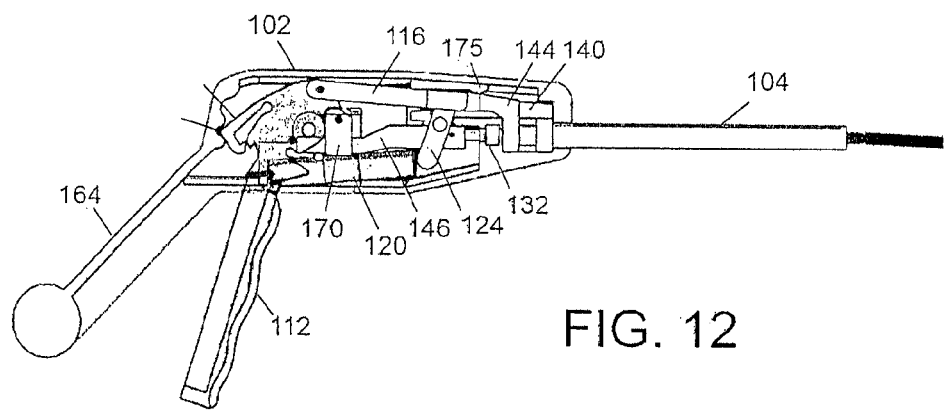
FIG. 12 depicts a housing and handle configuration after triggering release to fully compress the needle deployment member and advance the sheath, according to one embodiment.
Figure 13:
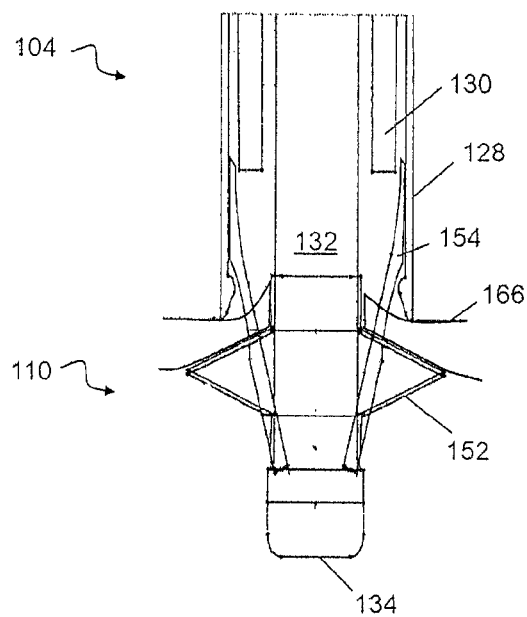
FIG. 13 schematically depicts the configuration of the needle deployment member after triggering release, according to one embodiment.

Full compression of needle deployment member 110 and simultaneous piercing of tissue wall 166 may be achieved in a reproducible, automatic manner by triggering release button 170, resulting in the configuration shown in FIG. 12. For example, triggering release button 170 disengages stop 168 and allows the tension stored in spring 120 to rotate lever 124, simultaneously withdrawing shaft 134 in a proximal direction while driving sheath 128 in a distal direction, each with respect to guide 132. Since handle 112 is positioned at the same location when charging spring 120 though the interaction of pawl 172 and recess 174, the amount of force that is released and used to drive shaft 134 and sheath 128 when button 170 is triggered may be predetermined and tailored to provide the desired piercing action of needles 154 through tissue wall 166. Although actuator 116 is now in contact with catcher extension 144, it has not yet caused relative movement of catcher 130 with respect to guide 132. Further, projection 175 on housing 102 may be configured to provide resistance to movement of catcher extension 144, so as to keep catcher 130 in its proximal position even as spring 120 drives sheath extension 140 distally. As shown in FIG. 13, movement of shaft 134 to its most proximal position has fully compressed needle deployment member 110 and has deflected wings 152 outwardly while positioning needles 154 at the desired piercing angle. Likewise, movement of sheath 128 to its most distal position sandwiches tissue wall 166 against wings 152 and causes needles 154 to pierce tissue wall 166 before entering the lumen of sheath 128.

Figure 14:
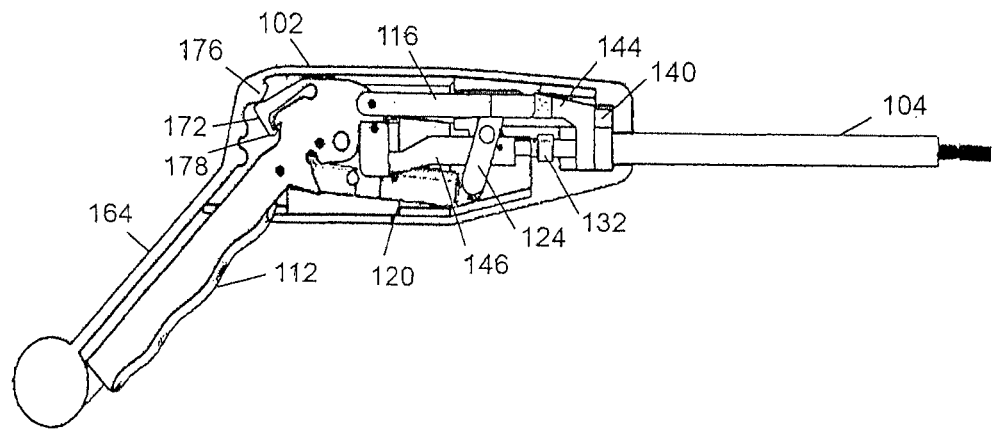
FIG. 14 depicts a housing and handle configuration after advancing the catcher, according to one embodiment.
Figure 15:
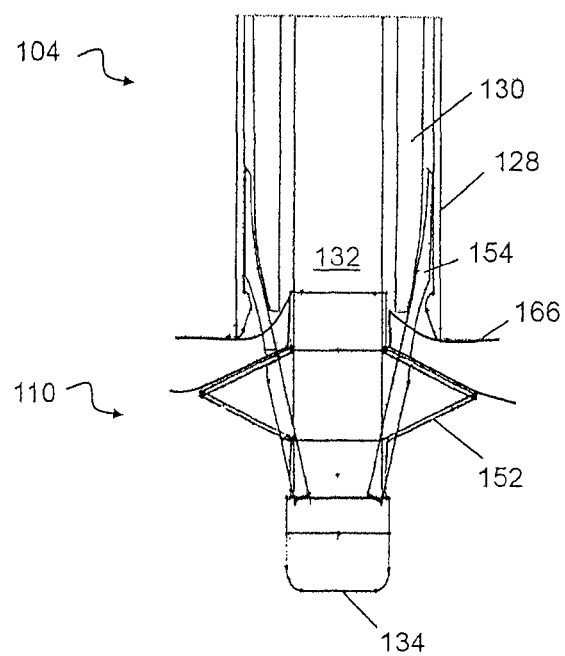
FIG. 15 schematically depicts the configuration of the needle deployment member after advancing the catcher, according to one embodiment.

After needles 154 have pierced tissue wall 166, handle 112 may be drawn to its full range of travel against grip 164 as shown in FIG. 14. Movement of handle 112 to this position drives actuator 116 against catcher extension 144, causing catcher 130 to move distally with respect to guide 132. This position of handle 112 also causes stop 176 to deflect pawl 172 towards handle 112, where it may be retained in the deflected position by hook 178. Engagement of hook 178 provides the user with an audible and tactile indication that handle 112 has traveled its full range of motion and correspondingly, that catcher 130 has been extended and captured needles 154. As shown in FIG. 15, catcher 130 captures needles 154 against sheath 128 when it is extended distally. Catcher 130 may be configured to provide sufficient friction in cooperation with sheath 128 to capture needles 154 when extended to its distal position to overcome any resistance of lower band 158, allowing needles 154 to be released from needle deployment member 110. If a needle 154 is not captured, it may be retained by lower band 158 and subsequently returned to a position against shaft 134 for removal.

Figure 16:
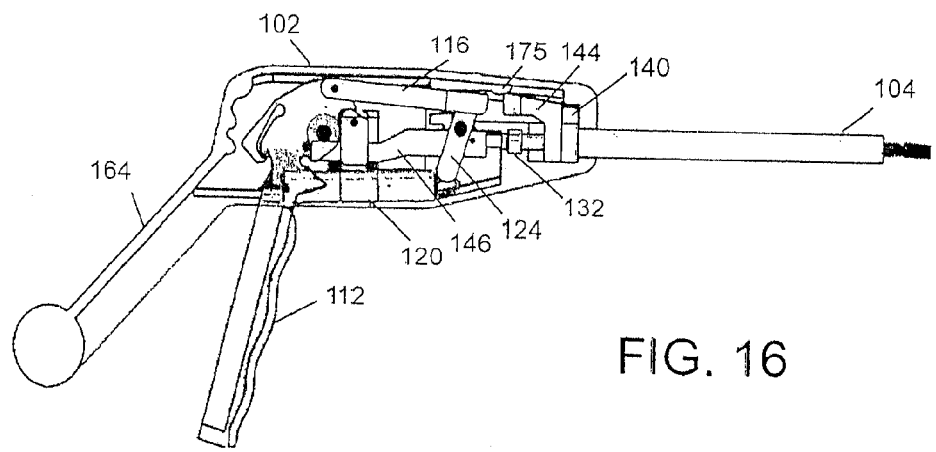
FIG. 16 depicts a housing and handle configuration after the handle is released, according to one embodiment.
Figure 17:
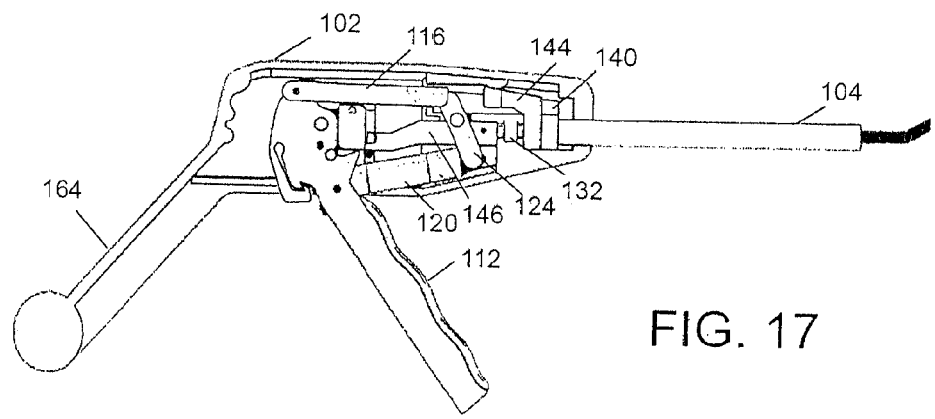
FIG. 17 depicts a housing and handle configuration after the needle deployment member is returned to the uncompressed configuration, according to one embodiment.
Figure 18:
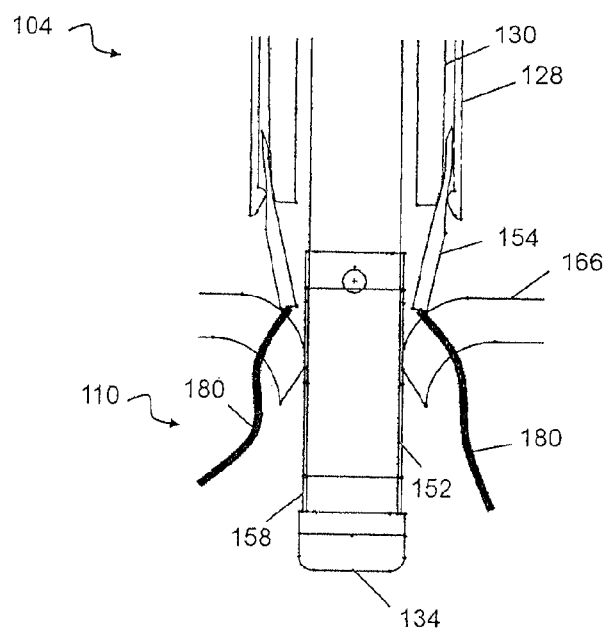
FIG. 18 schematically depicts the configuration of the needle deployment member after being returned to the uncompressed configuration, according to one embodiment.

Having reached the end of its stroke, handle 112 may be released and allowed to return to the configuration shown in FIG. 16 due to the tension in spring 120. In this embodiment, no significant movement of sheath 128, catcher 130 or shaft 134 may occur at this time. Projection 175 may provide resistance against catcher extension 144, helping to keep catcher 130 and sheath 128 in the distal positions. Since pawl 172 is secured in its deflected position by hook 178, it does not engage detent 174 and allows the user to complete the withdrawal sequence by moving handle 112 to match the position shown in FIG. 17 and decompress needle deployment member 110. For example, movement of handle 112 to the position furthest from grip 164 causes shaft extension 146 to drive shaft 134 to its most distal position with respect to guide 132. Simultaneously, shaft extension 146 rotates lever 124, causing sheath extension 140 and sheath 128 to be withdrawn. Interaction between sheath extension 140 and catcher extension 144 causes catcher 130 to be withdrawn in a coordinated manner. As a result, needle deployment member 110 is returned to its uncompressed configuration in which wings 152 are drawn against shaft 134. Since needles 154 are captured between sheath 128 and catcher 130, they are released from lower band 158 of needle deployment member 110 and withdrawn at the same time, pulling suture material 180 through tissue wall 166.

Figure 19:
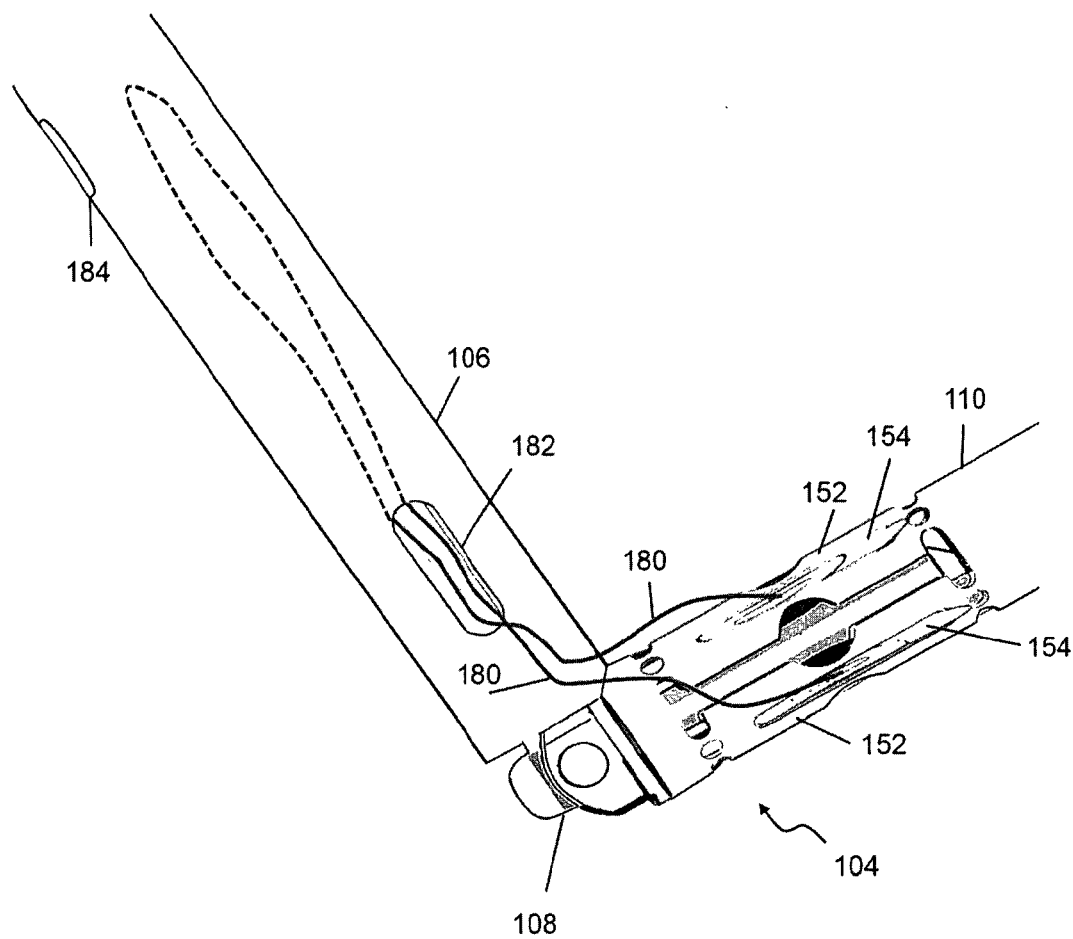
FIG. 19 depicts details of the connection between an elongated delivery member and a suture catheter, according to one embodiment.

Further details regarding the connection between suture catheter 106 and deployment member 104 are depicted in FIG. 19. As shown, hinge 108 may couple the distal end of deployment member 104 to suture catheter 106. As desired, hinge 108 may allow rotation in one direction up to approximately 90°. Rotation in the other direction may be restricted by a stop or other feature to increase pushability of suture catheter 106 when traversing through subcutaneous tissue and the vessel wall. Further, rotation in one direction helps align suture delivery device 100 with the sagittal plane of the vessel track, while allowing adjustments in insertion angle, such as in the range of approximately 45° to 90°. Hinge 108 may be rounded to minimize risk of damage to tissue during placement and while performing the procedure. Suture material 180 may extend from suture catheter 106 through one or more ports 182 and thread through needles 154. Suture catheter 106 may also include a guidewire port 184, such as a quick exchange port, to facilitate use of a guidewire when positioning suture delivery device 100 using techniques known in the art.

In other embodiments, suture catheter 106 may employ other suitable design configurations to facilitate access to patient's vessel. For example, suture catheter 106 may feature an ovalized diameter to preferentially permit flexing about the major axis. Further, the material used to form suture catheter 106 may be selected to provide the desired amount of flexibility of a given application. Suture catheter 106 may also exhibit a pre-bent configuration, having an angle of approximately 45° or any other suitable angle that may be indicated based on the desired application. As yet another example, one or more hinges may be provided in addition to hinge 108 to allow suture catheter 106 to take on a desired conformation. In one aspect, suitable modifications may be made to suture catheter 106 to facilitate access to smaller vessel diameters.

Figure 20:
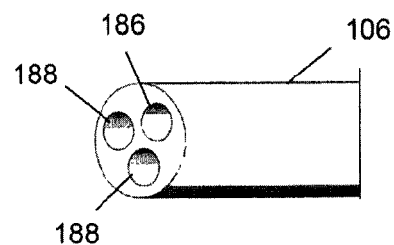
FIG. 20 depicts a partial cross section of the suture catheter, according to one embodiment.

A partial cross sectional view of suture catheter 106 is shown in FIG. 20. In this embodiment, suture catheter 106 has a guidewire lumen 186 that communicates with guidewire port 184 and two suture lumens 188 that communicate with suture ports 182. As desired, suture material 180 may be disposed within suture lumens in any suitable manner. For example, suture material 180 may be carried within suture cartridges that are then inserted in suture lumens 188, allowing ends of the suture material to extend out suture port 182 to thread through needle 154. The suture cartridge may be configured to mechanically or chemically apply suture tension when stored within suture catheter 106 to help prevent suture material 180 from being pulled out prematurely during insertion of suture delivery device 100. Each suture cartridge may have one or more lumens to allow varying lengths of suture material to be carried. For example, a single lumen cartridge may carry a suture having a length approximately the same as the length of the cartridge. When a plurality of lumens is employed, the length of carried suture material may be a multiple of the number of lumens.

Figures 21, 22:
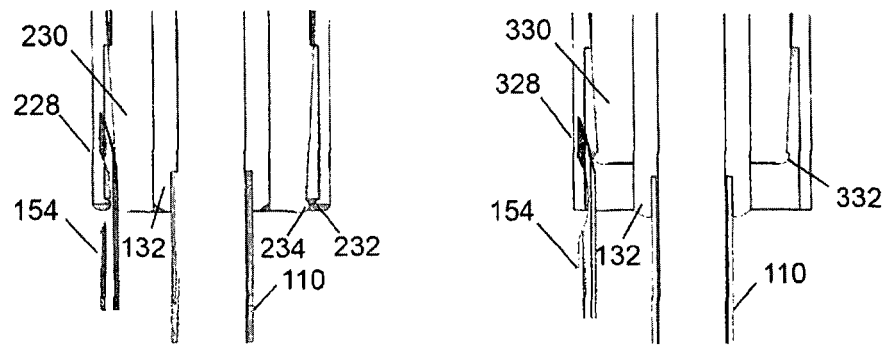
FIG. 21 depicts an alternative sheath and catcher configuration, according to one embodiment.
FIG. 22 depicts another alternative sheath and catcher configuration, according to one embodiment.

Using the techniques of the present disclosure, aspects of suture delivery device 100 may be embodied in other specific forms. For example, another design of catcher and sheath is depicted in FIG. 21. In this embodiment, sheath 228 and catcher 230 each have an annular rib, ribs 232 and 234 respectively to facilitate capture and retention of needles 154 when catcher 230 is extended distally. In another embodiment, instead of using ribs 232 and 234 to further enhance retention of the needs between catcher 230 and sheath 228, a material barrier may be implemented.

Figure 23:
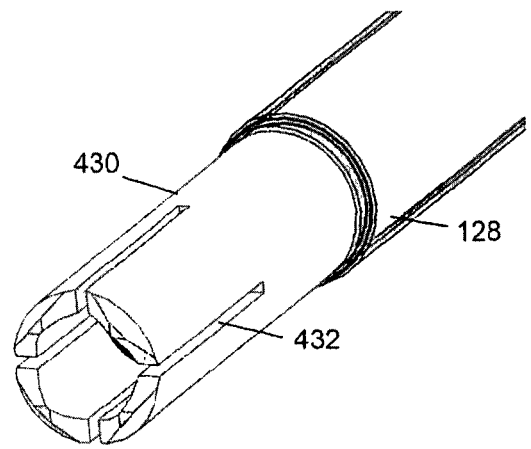
FIG. 23 depicts an alternative catcher configuration, according to one embodiment.

Alternatively, as shown in FIG. 22, catcher 330 may have an annular rib 332 and sheath 228 may exhibit a relatively straight profile. In yet another embodiment shown in FIG. 23, catcher 430 may have needle receiving slots 432 to capture needles 154. As will be appreciated, one slot may be configured for each needle and may have entrance features such as ramps or inclined planes to guide the needle into the slot. Slots 432 may be tapered to improve capture of needles 154.

The needles are deployed to penetrate tissue and in turn enter needle receiver/catcher. The needles may be retained in the needle catcher/receiver by friction. Friction may be provided by various designs, components, and materials. The needle catcher/receiver may be stationary during needle firing or may move distally towards the needle deployment member or may move proximally towards handle. A sheath may be used to guide needle movement (or define the needle movement boundary) along the device longitudinally towards proximal end. For example, friction capture of needle may be created by variable space between sheath and catcher. Space between sheath and catcher may be wider at needle entry and narrower at needle capture. Alternatively, space between sheath and catcher may be wider for needle entry and narrower for needle capture. In another example, the needle may be captured due to friction of interaction with material of the needle catcher/receiver or sheath while the space between sheath and needle catcher/receiver does not change longitudinally.

The needles may be captured in the needle catcher/receiver passively or actively. In the passive embodiment, there is no component movement or there is one component movement by either sheath or catcher/receiver. The variable space between the sheath and the catcher/receiver may be a fixed gradient. In addition, the space between sheath and catcher may be wider at distal end and narrower at proximal end. Thus, in one embodiment, the sheath and catcher/receiver remain stationary and the needles enter into space defined by sheath and the catcher/receiver. In other words, the needles move distally and are retained by the narrowing space between sheath and the needle catcher/receiver. In another embodiment of the passive method, the sheath moves distally to define space for receiving the needles. The needles enter into the space defined by the sheath and the catcher/receiver and are bound/guided by the sheath inner-wall. The needles move proximally and are retained by the narrowing space between the sheath and catcher/receiver. The sheath retracts proximally while the catcher/receiver remains stationary.

In the active embodiment, the space between the sheath and catcher/receiver may be a dynamic gradient. Relative motion between the sheath and receiver may change during needle movement proximally to create narrowing of inter-space between the sheath and needle catcher/receiver to capture and retain the needles. The sheath and catcher/receiver may move relative to each other to create more space for needle entry into inter-space. The sheath and receiver may move relative to each other to reduce the inter-space and capture the needles. In one embodiment, the space between the sheath and catcher/receiver is opened up while the sheath moves distally to receive the needles. The space between the sheath and catcher/receiver may be reduced by retracting the sheath proximally while the catcher/receiver moves distally, or by retracting the sheath proximally while the catcher/receiver remains stationary. In another embodiment, the sheath is positioned against soft tissue. The space between the sheath and catcher/receiver may be reduced to receive the needles by moving the catcher/receiver distally.

In another embodiment, the variable space between the sheath and catcher/receiver may include mechanical engagement to enhance capture and retention of the needles more securely. The sheath may move distally to define space for receiving the needles. The needles then enter the space defined by the sheath and the catcher/receiver. The needles move distally and are retained by the narrowing space between the sheath and catcher/receiver. The retention of the needles may be enhanced by mechanical compression to engage the needles. Finally, the sheath is retracted proximally while catcher/receiver remains stationary. On skilled in the art would recognize that other methods of ensuring needle capture and retention beyond those described herein may be implemented.

As described above, suture delivery device 100 may be employed to close openings formed in a body lumen or other tissue. One exemplary routine for employing device 100 may involve gaining access to a patient's vasculature, such as by using the Seldinger technique. As known to those of skill in the art, a Seldinger needle may be introduced into a patient's femoral artery at a suitable location on the thigh. A guidewire may be advanced through the Seldinger needle to locate a position within the artery, after which the Seldinger needle is removed. A dilator coaxially disposed within an introducer sheath may be advanced over the guidewire until the distal end of the dilator is positioned within the artery. After removal of the dilator, suture delivery device 100 may be advanced over guidewire, such as by threading suture catheter 106 over the proximal end of the guidewire, which may then exit though port 184. Once suture catheter 106 has entered the artery, the guidewire may be removed.

The distal end of delivery member 104 is then advanced until pulsatile blood is observed exiting from the proximal end of bleed back lumen 136, indicating needle deployment member 110 has been positioned inside the vessel, such that needles 154 are entirely within the femoral artery. Suture delivery device 100 may then be rotated along the vessel sagittal plane from 45° to 90°. The user may then operate handle 112 as indicated above with regard to FIGS. 7-18 to perform the suture placement sequence. As described, needle deployment member 110 is compressed while advancement of sheath 128 causes needles 154 to pierce tissue wall 166. Following capture of needles 154 between catcher 130 and sheath 128, suture material 180 is pulled through when needle deployment member 110 is decompressed. Successful completion of the suture placement sequence is indicated by a cessation of pulsatile blood flow from bleed back lumen 136. Suture delivery device 100 may then be rotated along the vessel sagittal plane from 90° to 45° and withdrawn, leaving suture material 180 deployed through tissue wall 166.

Figure 24:
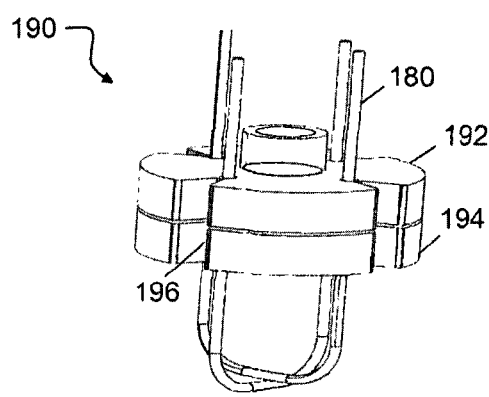
FIG. 24 depicts a suture locking device, according to one embodiment.

After deployment of suture material 180, any suitable percutaneous procedure may be performed through the opening. Upon completion of the procedure, suture material 180 may be tied or otherwise secured to approximate tissue around the opening. Suture material may be secured through use of sliding knots or other suitable techniques. As known in the art, clips, glue or interlocking devices may be used to secure the ends of suture material 180. For example, FIG. 24 depicts a suture locking device 190 that may be carried on the end of an elongated delivery member (not shown). Suture locking device 190 may feature an upper disc 192 and lower disc 194 that rotate with respect to each other. Upper disc 192 and lower disc 194 may have slots 164 that are aligned during delivery. Suture material 180 may be fed through slots 196 and suture locking device 190 may be advanced to a desired position to tension the suture. Subsequent rotation of upper disc 192 and lower disc 194 with respect to each other secures suture material 180 by friction.

Embodiments have been described above in the context of suture delivery device 100 that features automatic and coordinated operation of handle 112 to produce relative movement between tubular sheath 128, catcher 130, guide 132 and shaft 134 to expand needle deployment member 110, sandwich tissue between needle deployment member 110 and sheath 128, pierce the tissue with needles 154 and subsequently catch the needles. As will be appreciated, any of these operations or combinations of these operations may be performed independently. One exemplary embodiment is shown in FIG. 25 as suture delivery device 500. Housing 502 may include proximal actuator 504 that slides to create relative movement at a distal region 506 to create a conformation change between a reduced profile for insertion and an expanded profile that helps stabilize tissue for suture delivery. Handle 508 may be withdrawn to charge springs inside handle 502 (not shown) and to provide relative motion between distal region 506 and proximal region 510 to engage tissue between these elements as described above. Button 512 may release spring tension stored by housing 502 to pierce the tissue and place the sutures. In turn, FIG. 26 shows a detail of a needle pushing element 514 that may be driven proximally upon release of button 512 to place sutures 516 and 518. Capture of needles 520 may be achieved using any suitable technique, such as in the embodiments described above.

In general, a suture delivery device embodying aspects of this disclosure may include suitable elements to produce relative movement between a proximal region of the device and the expanded profile region, allowing tissue to be secured between the regions and provide a target for needle-deployed sutures carried by the device. Such relative movement between the distal region and the proximal region may involve movement of the distal region towards the proximal region, movement of the proximal region towards the distal region, or both. Further, aspects involving the placement of the sutures, including one or more of the deployment of the distal region, deployment of the proximal region, securing tissue between the distal and proximal regions, firing of the needles to place the sutures, capture of the needles after passing through the secured tissue, retraction of the deployed regions before withdrawal and withdrawal of the device may be performed independently or in combination with others.

Embodiments described above have generally been in the context of an expanding distal region formed by needle deployment member 110. However, as will be appreciated, any suitable structure that may undergo a conformational change from a reduced profile for insertion to an expanded profile for stabilizing tissue during suture placement may be used. As such, a mechanical foot or base may be used as desired. In another aspect, an inflatable balloon may be employed as depicted in FIG. 27. Catheter 600 may be integrated with needle actuating and capturing elements described above and includes a distal expanding region in the form of balloon 602. The expanded profile of balloon 602 is shown in phantom and may be achieve by use of a suitable inflation fluid. Catheter 600 may employ a multi-lumen configuration to provide communication for the inflation fluid. Further, a bleed back lumen may be in communication with distal port 604 to facilitate correct positioning of balloon 602 within a patient's vessel. Catheter 600 may feature an atraumatic distal tip 606 to facilitate introduction.

Another aspect of this disclosure involves needle and suture designs. The embodiments described above have been in the context of a one-piece needle design. Alternatively, a detachable needle tip carrying the suture may be employed. As shown in FIG. 28, a suitable design may feature a needle base 700 having a detachable tip 702 carrying suture 704. Tip 702 may have a recess configured to fit over post 706 to secure the tip and suture during deployment and delivery. Subsequently, needle base 700 may be retained, such as by lower band 158 while tip 702 is captured, such as by interaction between sheath 128 and catcher 130. Post 706 may have an asymmetrical configuration, such as with ribs 708, to retain tip 702 in a desired rotational orientation. In another embodiment, the needle tip may include a post that is received by a matching receptacle in the needle base.

When suture carried tip 702 and needle base 700 enter into spacing between sheath and catcher/receiver at the end of needle piercing, needle base 700 may be retracted to distal end of device while suture carried tip 702 is retained in the space created by sheath and catcher/receiver.

Described herein are certain exemplary embodiments. However, one skilled in the art that pertains to the present embodiments will understand that the principles of this disclosure can be extended easily with appropriate modifications to other applications.

What is claimed is:

1. A suture delivery device for percutaneously suturing tissue comprising:
   an elongated deployment member having a guide member coaxially disposed over a shaft member;
   a needle deployment member carried at a distal end of the elongated deployment member, the needle deployment member having at least one deflectable wing, wherein a proximal end of the needle deployment member is secured to the guide member and a distal end of the needle deployment member is secured to the shaft member; and
   a plurality of needles releasably secured to the needle deployment member, wherein the needle deployment member is configured to transition between an uncompressed configuration corresponding to a first distance between the proximal and distal ends that longitudinally aligns the plurality of needles with the shaft member and a compressed configuration corresponding to a second distance between the proximal and distal ends that positions the plurality of needles at a piercing angle in a proximal direction, the first distance being greater than the second distance, wherein each of the at least one deflectable wing has a longitudinal slot formed therein to axially retain one of the plurality of needles and wherein a distal end of each needle remains at a same radial distance from the shaft member when transitioning from the uncompressed configuration to the compressed configuration.

2. The suture delivery device of claim 1, wherein relative longitudinal movement of the shaft member with respect to the guide member transitions the needle deployment member between the uncompressed and compressed configurations.

3. The suture delivery device of claim 2, wherein the elongated deployment member further comprises a sheath member coaxially disposed over the guide member, the sheath member configured to extend over a proximal portion of the plurality of needles positioned at the piercing angle when the sheath member is advanced distally over the guide member.

4. The suture delivery device of claim 3, wherein the elongated deployment member further comprises a catcher member coaxially disposed between the guide member and the sheath member, the catcher member configured to capture the plurality of needles positioned at the piercing angle when the catcher member is advanced distally over the guide member.

5. The suture delivery device of claim 4, further comprising a housing at a proximal end of the elongated deployment member configured to provide relative longitudinal movement between the guide member and each of the sheath member, the catcher member and the shaft member.

6. The suture delivery device of claim 5, wherein the housing is configured to store a reproducible amount of tension that may be selectively released to simultaneously move the sheath member distally with respect to the guide member and the shaft member proximally with respect to the guide member.

7. The suture delivery device of claim 4, wherein at least one of the plurality of needles comprises a needle base and a detachable tip disposed on the needle base, the detachable tip being captured by the catcher member.

8. The suture delivery device of claim 1, wherein the needle deployment member further comprises a lower band configured to retain a non-piercing end of each of the plurality of needles and an upper band configured to position the plurality of needles at the piercing angle when in the compressed configuration.

9. The suture delivery device of claim 1, further comprising a suture catheter secured to the distal end of the elongated deployment member, wherein the suture catheter is configured to carry suture material that may be threaded through the plurality of needles.

10. The suture delivery device of claim 9, wherein the suture catheter is secured to the elongated deployment member by a hinge allowing rotation in one direction.

11. A method for delivering a suture percutaneously comprising:
providing an elongated deployment member having a guide member coaxially disposed over a shaft member, a needle deployment member carried at a distal end of the elongated deployment member, the needle deployment member having at least one deflectable wing, wherein a proximal end of the needle deployment member is secured to the guide member and a distal end of the needle deployment member is secured to the shaft member and a plurality of needles releasably secured to the needle deployment member;
advancing the elongated deployment member percutaneously to a desired position in a patient; and
withdrawing the shaft proximally relative to the guide member to transition the needle deployment member from an uncompressed configuration that longitudinally aligns the plurality of needles with the shaft member to a compressed configuration that extends the at least one deflectable wing and positions the plurality of needles at a piercing angle in a proximal direction, wherein each of the at least one deflectable wing has a longitudinal slot formed therein to axially retain one of the plurality of needles and wherein a distal end of each needle remains at a same radial distance from the shaft member when transitioning from the uncompressed configuration to the compressed configuration.

12. The method of claim 11, wherein the elongated deployment member further comprises a sheath member coaxially disposed over the guide member, further comprising advancing the sheath member distally over the guide member to extend over a proximal portion of the plurality of needles positioned at the piercing angle to cause the plurality of needles to pierce tissue sandwiched between the extended deflectable wings and a distal end of the sheath.

13. The method of claim 12, wherein advancing the sheath member distally over the guide member and withdrawing the shaft member proximally within the guide member is performed simultaneously.

14. The method of claim 13, wherein advancing the sheath member distally and withdrawing the shaft member proximally is performed by applying an automatically reproducible amount of force.

15. The method of claim 12, wherein the elongated deployment member further comprises a catcher member coaxially disposed between the guide member and the sheath member, further comprising advancing the catcher member distally over the guide member to capture the plurality of needles positioned at the piercing angle.

16. The method of claim 15, wherein the needles are captured by friction between the distal end of the sheath and a distal end of the catcher member, further comprising a housing at a proximal end of the elongated deployment member configured to provide relative longitudinal movement between the guide member and each of the sheath member, the catcher member and the shaft member.

17. The method of claim 16, further comprising advancing the shaft member distally with respect to the guide member after the plurality of needles are captured to transition the needle deployment member to the uncompressed configuration.

18. The method of claim 17, further comprising simultaneously withdrawing the sheath member and the catcher member proximally with respect to the guide member after the plurality of needles are captured.

19. The method of claim 18, further comprising carrying suture material threaded through each of the plurality of needles in a suture catheter secured to the distal end of the elongated delivery member.

20. The method of claim 19, wherein withdrawing the sheath member and the catcher member draws the suture material through the tissue.

* * * * *